United States Patent
Habib et al.

(10) Patent No.: US 7,875,291 B1
(45) Date of Patent: *Jan. 25, 2011

(54) COMPOSITION FOR MANAGING DIABETES, OBESITY, AND HYPERLIPIDEMIA AND ASSOCIATED METHODS

(75) Inventors: Amid Habib, Altamonte Springs, FL (US); Samuel E. Crockett, Orlando, FL (US); Claude T. Isler, Orlando, FL (US); Sam Pratt, Altamonte Springs, FL (US)

(73) Assignee: Glu-Pro, Inc., Altamonte Springs, FL (US)

( * ) Notice: Subject to any disclaimer, the term of this patent is extended or adjusted under 35 U.S.C. 154(b) by 508 days.

This patent is subject to a terminal disclaimer.

(21) Appl. No.: 12/015,542

(22) Filed: Jan. 17, 2008

Related U.S. Application Data

(63) Continuation-in-part of application No. 10/933,202, filed on Sep. 2, 2004, now Pat. No. 7,332,181.

(60) Provisional application No. 60/500,652, filed on Sep. 5, 2003.

(51) Int. Cl.
- *A61K 9/14* (2006.01)
- *A61K 9/48* (2006.01)
- *A61K 47/00* (2006.01)
- *A61M 36/14* (2006.01)
- *A23L 1/30* (2006.01)

(52) U.S. Cl. .................. 424/451; 424/1.73; 424/72; 424/73; 424/439; 424/489

(58) Field of Classification Search ............... None
See application file for complete search history.

(56) References Cited

U.S. PATENT DOCUMENTS

| | | | |
|---|---|---|---|
| 5,922,704 A | 7/1999 | Bland | |
| 5,952,295 A | 9/1999 | Arnaud-Battandier et al. | |
| 5,980,905 A * | 11/1999 | de la Harpe et al. | ......... 424/769 |
| 6,063,820 A | 5/2000 | Cavazza | |
| RE37,020 E | 1/2001 | Lin et al. | |
| 6,291,533 B1 | 9/2001 | Fleischner | |
| 6,365,176 B1 | 4/2002 | Bell et al. | |
| 6,417,233 B1 | 7/2002 | Sears et al. | |
| 6,479,544 B1 | 11/2002 | Horrobin | |
| 6,479,545 B1 | 11/2002 | Levinson et al. | |
| 7,169,416 B2 | 1/2007 | Koss et al. | |
| 2001/0031744 A1 | 10/2001 | Kosbab | |
| 2002/0025983 A1 | 2/2002 | Horrobin | |
| 2002/0044957 A1 | 4/2002 | Fuchs et al. | |
| 2002/0136711 A1 | 9/2002 | Cochran | |
| 2002/0172721 A1 | 11/2002 | Boulos et al. | |
| 2002/0192346 A1 | 12/2002 | Cavazza | |
| 2003/0031753 A1 | 2/2003 | Watkins et al. | |
| 2003/0050341 A1 | 3/2003 | Bydlon et al. | |

FOREIGN PATENT DOCUMENTS

JP     60-248610     12/1985

* cited by examiner

*Primary Examiner*—S. Tran
(74) *Attorney, Agent, or Firm*—Jacqueline E. Hartt; Lowndes, Drosdick, Doster, Kantor & Reed, P.A.

(57) ABSTRACT

A nutritional supplement includes a first formulation including minerals: chromium polynicotinate, magnesium glycinate, manganese sulfate, selenium, vanadyl sulfate, zinc gluconate, copper gluconate, iodine, and boron; and vitamins: vitamins C, B1, B2, B3, B6, B12, and D, biotin, alpha-lipoic acid, and folic acid. The second formulation, packaged separately from the first, includes essential fatty acids: evening primrose oil, flax seed oil, sunflower oil, sesame seed oil, and pumpkin seed oil; and vitamins: vitamin E and vitamin Q-10. A method for improving metabolic function includes consuming the first and second formulation. A method of formulating a composition for improving metabolic function includes packaging together the first formulation and packaging together and separately from the first formulation the second formulation. A method for assisting a patient to improve metabolic function includes prescribing the first formulation and the second formulation to be taken separately from the first formulation.

2 Claims, No Drawings

COMPOSITION FOR MANAGING DIABETES, OBESITY, AND HYPERLIPIDEMIA AND ASSOCIATED METHODS

CROSS-REFERENCE TO RELATED APPLICATIONS

This application is a continuation-in-part of application Ser. No. 10/933,202, filed Sep. 2, 2004, which itself claimed priority to provisional application 60/500,652, filed Sep. 5, 2003.

BACKGROUND OF THE INVENTION

1. Field of the Invention

The present invention relates to nutritional compositions and methods for managing metabolic disorders, and, more particularly, to such nutritional compositions and methods for managing diabetes, obesity, and hyperlipidemia.

2. Description of Related Art

Interest in nutritional supplements for managing various diseases/disorders has been rapidly increasing as the link between such states and metabolic balance has been recognized in the medical community. While the need for certain vitamins is well established, less is known about bodily requirements for essential fatty acids and minerals. As vitamins are by definition necessary for proper metabolic functioning, essential fatty acids and minerals are also needed; however, the proper doses and proportions have not been definitively established.

The need for these essential fatty acids and minerals has become increasingly acute owing to modern dietary habits, cooking methods, and soil depletion. Cooking may, for example, destroy essential fatty acids, and many modern consumers are likely deficient in certain "good" fatty acids, particularly omega-3 ($\omega_3$) and omega-6 ($\omega_6$) fatty acids. Overfarming by agribusinesses has also led to soils that are depleted of essential minerals, so that, even if one attempts to "eat right," the foods that are recommended as being beneficial may not contain an appreciable concentration of minerals.

The cases of obesity, diabetes, and hyperlipidemia in the population have been on an ever-increasing pathway; therefore, there is a need to address underlying nutritional issues in order to ameliorate this trend.

In an attempt to assist diabetic patients manage their disease a formulation was developed by the present inventor and tested on 15 patients having type-I diabetes. This formulation, detailed in Table 1, resulted in an efficacy of 50% to lower HbA1c levels, as determined in a year-long, double-blind, placebo-controlled trial. All patients showed a decrease in total cholesterol and low-density lipoprotein (LDL) levels and an increase in high-density lipoprotein (HDL) levels.

TABLE 1

Initial Vitamin and Mineral Formulation

| Ingredient | Daily dose[a] | Dose per capsule |
| --- | --- | --- |
| Chromium polynicotinate | 200 mcg | 100 mcg |
| Magnesium oxide | 100 mg | 50 mg |
| Magnesium aspartate | 30 mg | 15 mg |
| Selenium | 50 mcg | 25 mcg |
| Vanadium sulfate | 6 mg | 3 mg |
| Zinc gluconate | 20 mg | 10 mg |
| Vitamin C | 250 mg | 125 mg |

TABLE 1-continued

Initial Vitamin and Mineral Formulation

| Ingredient | Daily dose[a] | Dose per capsule |
| --- | --- | --- |
| Vitamin E | 200 U | 100 U |
| Vitamin B1 (thiamine) | 15 mg | 7.5 mg |
| Vitamin B2 (riboflavin) | 20 mg | 10 mg |
| Vitamin B3 (niacin) | 20 mg | 10 mg |
| Vitamin B6 (pyridoxine) | 20 mg | 10 mg |
| Vitamin B12 (cobalamine) | 500 mcg | 250 mcg |
| Folic acid | 400 mcg | 200 mcg |
| Alpha-lipoic acid | 120 mg | 60 mg |

[a]Dosage = one capsule after meals, twice daily.

While this formulation was extremely effective, it was deemed important to improve upon the formulation and method of delivery.

SUMMARY OF THE INVENTION

The present invention is directed to a nutritional supplement and associated methods. In a preferred embodiment, the supplement composition comprises a first and a second formulation. The first formulation is packaged together and comprises a plurality of minerals, including chromium polynicotinate, magnesium glycinate, manganese sulfate, selenium, vanadium (as vanadyl sulfate), zinc (as zinc gluconate), copper (as copper gluconate), iodine, and boron; and a plurality of vitamins, including vitamin C, vitamin B1, vitamin B2, vitamin B3, vitamin B6, vitamin B12, biotin, vitamin D, folic acid, and a vitamin-like antioxidant, alpha-lipoic acid.

The second formulation is also packaged together, and is packaged separately from the first formulation packaging. The second formulation comprises a plurality of essential fatty acids, including walnut or evening primrose oil, flax seed oil, safflower or sunflower oil, sesame seed oil, and pumpkin seed oil; and other components, including vitamin E and vitamin Q-10.

It will be understood by one of skill in the art that other elements in these compositions may be added or substituted without departing from the spirit of the invention, for example, in the second formulation, other oils such as cod liver oil may also be used.

Another aspect of the invention is directed to a method for improving metabolic function in a human. This method comprises the steps of consuming the first and the second formulation.

A further aspect of the invention is directed to a method of formulating a composition for improving metabolic function in a human. This method comprises the steps of packaging together the first formulation and packaging together and separately from the first formulation the second formulation.

An additional aspect of the invention is directed to a method for assisting a patient to improve metabolic function comprising the steps of prescribing the first formulation to the patient, and prescribing the second formulation to the patient to be taken separately from the first formulation.

The features that characterize the invention, both as to organization and method of operation, together with further objects and advantages thereof, will be better understood from the following description. These and other objects attained, and advantages offered, by the present invention will become more fully apparent as the description that now follows is read.

DETAILED DESCRIPTION OF THE PREFERRED EMBODIMENTS

A description of the preferred embodiments of the present invention will now be presented. In a first preferred embodiment of the composition, the supplement comprises a first and a second formulation as tabulated in Tables 2 and 3. The first formulation has substantially no oil-soluble ingredients; the second formulation contains essential fatty acids in a believed preferred ratio of $\omega_6$ to $\omega_3$ concentrations of 2 to 1 or less, in particular, in a range of approximately 1:1-2:1, vitamin E, and vitamin Q-10.

TABLE 2

First Formulation for First Embodiment - Preferred Doses, with Acceptable Ranges Shown in Parentheses

| Ingredient | Daily dose | Dose per capsule |
|---|---|---|
| Chromium polynicotinate | 500 (200-1500) mcg | 250 (100-750) mcg |
| Magnesium glycinate | 250 (100-1500) mg | 125 (50-750) mg |
| Manganese (sulfate) | 5 (2-10) mg | 2.5 (1-5) mg |
| Selenium | 100 (25-200) mcg | 50 (12.5-100) mcg |
| Vanadium (vanadyl sulfate) | 10 (5-50) mg | 5 (2.5-25) mg |
| Zinc (gluconate) | 50 (10-70) mg | 25 (5-35) mg |
| Copper (gluconate) | 3 (2-5) mg | 1.5 (1-2.5) mg |
| Iodine | 100 (50-250) mcg | 50 (25-125) mcg |
| Boron | 3 (1-5) mg | 1.5 (0.5-2.5) mg |
| Vitamin C | 100 (50-1000) mg | 50 (25-500) mg |
| Vitamin B1 (thiamine) | 40 (10-200) mg | 20 (5-100) mg |
| Vitamin B2 (riboflavin) | 40 (10-200) mg | 20 (5-100) mg |
| Vitamin B3 (niacin) | 40 (10-200) mg | 20 (5-100) mg |
| Vitamin B6 (pyridoxine) | 20 (10-50) mg | 10 (5-25) mg |
| Vitamin B12 (cobalamin) | 1000 (100-10,000) mcg | 500 (50-5000) mcg |
| Biotin | 3 (1-5) mg | 1.5 (0.5-2.5) mg |
| Folic acid | 800 (200-5000) mcg | 400 (100-2500) mcg |
| Alpha-lipoic acid | 120 (10-1000) mg | 60 (5-500) mg |

TABLE 3

Second Formulation for First Embodiment

| Ingredient | Daily dose | Dose per capsule |
|---|---|---|
| Vitamin E | 400 (100-1200) U | 100 (25-300) U |
| Vitamin Q-10 | 120 (20-1000) mg | 30 (5-250) mg |
| Walnut oil | 600 (100-1000) mg | 150 (25-250) mg |
| Flax seed oil | 600 (100-1000) mg | 150 (25-250) mg |
| Pumpkin seed oil | 600 (100-1000) mg | 150 (25-250) mg |
| Safflower oil | 600 (100-1000) mg | 150 (25-250) mg |
| Sesame seed oil | 600 (100-1000) mg | 150 (25-250) mg |

Again, in a second preferred embodiment of the composition, the supplement comprises a first and a second formulation as tabulated in Tables 4 and 5. As above, the first formulation has substantially no oil-soluble ingredients; the second formulation contains essential fatty acids in a believed preferred ratio of $\omega_6$ to $\omega_3$ concentrations of 2 to 1 or less, in particular, in a range of approximately 1:1-2:1, vitamin E, and vitamin Q-10.

TABLE 4

First Formulation for Second Embodiment - Preferred Doses, with Acceptable Ranges Shown in Parentheses

| Ingredient | Daily dose | Dose per capsule |
|---|---|---|
| Chromium polynicotinate | 500 (200-1500) mcg | 250 (100-750) mcg |
| Magnesium glycinate | 250 (100-1500) mg | 125 (50-750) mg |
| Manganese (sulfate) | 5 (2-10) mg | 2.5 (1-5) mg |
| Selenium | 100 (25-200) mcg | 50 (12.5-100) mcg |
| Vanadium (vanadyl sulfate) | 10 (5-50) mg | 5 (2.5-25) mg |
| Zinc (gluconate) | 50 (10-70) mg | 25 (5-35) mg |
| Copper (gluconate) | 3 (2-5) mg | 1.5 (1-2.5) mg |
| Iodine | 100 (50-250) mcg | 50 (25-125) mcg |
| Boron | 3 (1-5) mg | 1.5 (0.5-2.5) mg |
| Vitamin C | 100 (50-1000) mg | 50 (25-500) mg |
| Vitamin B1 (thiamine) | 40 (10-200) mg | 20 (5-100) mg |
| Vitamin B2 (riboflavin) | 40 (10-200) mg | 20 (5-100) mg |
| Vitamin B3 (niacin) | 40 (10-200) mg | 20 (5-100) mg |
| Vitamin B6 (pyridoxine) | 20 (10-50) mg | 10 (5-25) mg |
| Vitamin B12 (cobalamin) | 1000 (100-10,000) mcg | 500 (50-5000) mcg |
| Biotin | 3 (1-5) mg | 1.5 (0.5-2.5) mg |
| Vitamin D | 400 (100-1000) U | 200 (50-500) U |
| Folic acid | 800 (200-5000) mcg | 400 (100-2500) mcg |
| Alpha-lipoic acid | 120 (10-1000) mg | 60 (5-500) mg |

TABLE 5

Second Formulation for Second Embodiment

| Ingredient | Daily dose | Dose per capsule |
|---|---|---|
| Vitamin E | 400 (100-1200) U | 100 (25-300) U |
| Vitamin Q-10 | 120 (20-1000) mg | 30 (5-250) mg |
| Evening primrose oil | 500 (100-1000) mg | 125 (25-250) mg |
| Flax seed oil | 1200 (100-1500) mg | 300 (25-375) mg |
| Pumpkin seed oil | 400 (100-1000) mg | 100 (25-250) mg |
| Sesame seed oil | 200 (100-1000) mg | 50 (25-250) mg |
| Sunflower oil | 700 (100-1000) mg | 175 (25-250) mg |

In a preferred embodiment, the ingredients of the first and the second formulation of the first and the second embodiments are packaged into capsules, each capsule containing the amount of ingredient listed in the third columns, headed "dose per capsule."

Preferably the doses are prescribed and consumed according to the following schedule: one capsule of the first formulation taken by mouth after a meal, twice daily; two capsules of the second formulation taken by mouth 15 minutes prior to a meal, twice daily.

Also preferably, for increasing compliance and ease of use, the capsules are placed into a package for daily consumption, such as using cardboard and burst containers such as are known in the art, each package containing two first formulation capsules and four second formulation capsules, labeled for time of consumption as indicated above.

The present inventions have been shown to decrease the patient's craving for sweets, decrease the patient's "carboholic" state, increase energy, improve glucose metabolism, and decrease cholesterol levels. It is believed that the composition of the present invention may inhibit the onset of type-II diabetes mellitus.

In a preferred embodiment, the ingredients of the first and the second formulation are packaged into capsules, each capsule containing the amount of ingredient listed in the third columns, headed "dose per capsule."

Preferably the doses are prescribed and consumed according to the following schedule: one capsule of the first formulation taken by mouth after a meal, twice daily; two capsules of the second formulation taken by mouth 15 minutes prior to a meal, twice daily.

Also preferably, for increasing compliance and ease of use, the capsules are placed into a package for daily consumption, such as using cardboard and burst containers such as are known in the art, each package containing two first formulation capsules and four second formulation capsules, labeled for time of consumption as indicated above.

As stated above, the present inventions have been shown to decrease the patient's craving for sweets, decrease the patient's "carboholic" state, increase energy, improve glucose metabolism, and decrease cholesterol levels. It is believed that the composition of the present invention may inhibit the onset of type II diabetes, will assist in managing types-I and -II diabetes, obesity, hyperlipidemia, and chronic fatigue syndrome, and in lowering cardiovascular risk.

It will be understood by one of skill in the art that alternate forms of packaging/delivery may be contemplated. For example, the first formulation may be packaged as a nutritional bar, and the second formulation may be incorporated into condiments such as a salad dressing, mayonnaise, margarine or spread, or as a nutritional shake or other type of drink.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the composition and methods described herein are by way of example, and the scope of the invention is not limited to the exact details thereof.

What is claimed is:

1. A nutritional supplement composition for improving metabolic function in a human comprising:
    a first formulation comprising, packaged together, a plurality of minerals, including chromium polynicotinate, magnesium glycinate, manganese sulfate, selenium, vanadium, zinc, copper, iodine, and boron; and a plurality of vitamins, including vitamin C, vitamin B1, vitamin B2, vitamin B3, vitamin B6, vitamin B12, vitamin D, biotin, alpha-lipoic acid, and folic acid; and
    a second formulation comprising, packaged together separately from the first formulation packaging, a plurality of essential fatty acids, including evening primrose oil, flax seed oil, sunflower oil, sesame seed oil, and pumpkin seed oil; and a plurality of vitamins, including vitamin E and vitamin Q-10 wherein the components of the first and the second formulations are present in approximate ranges for achieving a daily dose of:
    minerals in the first formulation: chromium polynicotinate, 200-1500 mcg; magnesium glycinate, 100-1500 mg; manganese sulfate, 2-10 mg; selenium, 25-200 mcg; vanadium, 5-50 mg; zinc, 10-70 mg; copper, 2-5 mg; iodine, 50-250 mcg; and boron, 1-5 mg;
    vitamins in the first formulation: vitamin C, 50-1000 mg; vitamin B1, 10-200 mg; vitamin B2, 10-200 mg; vitamin B3, 10-200 mg; vitamin B6, 10-50 mg; vitamin B12, 100-10,000 mcg; biotin, 1-5 mg; vitamin D, 100-1000 U; alpha-lipoic acid, 100-1000 mg; and folic acid, 200-5000 mcg;
    essential fatty acids in the second formulation: evening primrose oil, 100-1000 mg; flax seed oil, 100-1500 mg; sunflower oil, 100-1000 mg; sesame seed oil, 100-1000 mg; and pumpkin seed oil, 100-1000 mg; and
    vitamins in the second formulation: vitamin E, 100-1200 U; and vitamin Q-10, 20-1000 mg.

2. A method of formulating a composition for improving metabolic function in a human comprising the steps of:
    packaging together a first formulation comprising a plurality of minerals, including chromium polynicotinate, magnesium glycinate, manganese sulfate, selenium, vanadium (as vanadyl sulfate), zinc (as zinc gluconate), copper (as copper gluconate), iodine, and boron; and a plurality of vitamins, including vitamin C, vitamin B1, vitamin B2, vitamin B3, vitamin B6, vitamin B12, biotin, vitamin D, folic acid, and alpha-lipoic acid; and
    packaging together and separately from the first formulation a second formulation comprising a plurality of essential fatty acids, including evening primrose oil, flax seed oil, sunflower oil, sesame seed oil, and pumpkin seed oil; and a plurality of vitamins, including vitamin E and vitamin Q-10 wherein the first and the second formulation packaging steps comprise packaging the components thereof in approximate ranges for achieving a daily dose of:
    minerals in the first formulation: chromium polynicotinate, 200-1500 mcg; magnesium glycinate, 100-1500 mg; manganese sulfate, 2-10 mg; selenium, 25-200 mcg; vanadium, 5-50 mg; zinc, 10-70 mg; copper, 2-5 mg; iodine, 50-250 mcg; and boron, 1-5 mg;
    vitamins in the first formulation: vitamin C, 50-1000 mg; vitamin B1, 10-200 mg; vitamin B2, 10-200 mg; vitamin B3, 10-200 mg; vitamin B6, 10-50 mg; vitamin B12, 100-10,000 mcg; biotin, 1-5 mg; vitamin D, 100-1000 U; alpha-lipoic acid, 100-1000 mg; and folic acid, 200-5000 mcg;
    essential fatty acids in the second formulation: evening primrose oil, 100-1000 mg; flax seed oil, 100-1500 mg; sunflower oil, 100-1000 mg; sesame seed oil, 100-1000 mg; and pumpkin seed oil, 100-1000 mg; and
    vitamins in the second formulation: vitamin E, 100-1200 U; and vitamin Q-10, 20-1000 mg.

* * * * *